United States Patent
Qazi et al.

(10) Patent No.: US 9,999,769 B2
(45) Date of Patent: Jun. 19, 2018

(54) EXCITATION MODELING AND MATCHING

(71) Applicant: Cochlear Limited, Macquarie University, NSW (AU)

(72) Inventors: Obaid ur Rehman Qazi, Mechelen (BE); Bastiaan van Dijk, Deurne (BE)

(73) Assignee: Cisco Technology, Inc., San Jose, CA (US)

( * ) Notice: Subject to any disclaimer, the term of this patent is extended or adjusted under 35 U.S.C. 154(b) by 5 days.

(21) Appl. No.: 14/324,388

(22) Filed: Jul. 7, 2014

(65) Prior Publication Data
US 2015/0251006 A1   Sep. 10, 2015

Related U.S. Application Data

(60) Provisional application No. 61/950,316, filed on Mar. 10, 2014.

(51) Int. Cl.
A61N 1/36 (2006.01)
G06F 19/12 (2011.01)
A61N 1/05 (2006.01)

(52) U.S. Cl.
CPC ..... A61N 1/36032 (2013.01); A61N 1/36036 (2017.08); A61N 1/0541 (2013.01)

(58) Field of Classification Search
CPC .......................... A61N 1/36032; A61N 1/0541
USPC .......................................................... 607/57
See application file for complete search history.

(56) References Cited

U.S. PATENT DOCUMENTS

| 6,594,525 | B1 | 7/2003 | Zierhofer |
| 6,600,955 | B1 | 7/2003 | Zierhofer |
| 7,209,789 | B2 | 4/2007 | Zierhofer |
| 7,321,797 | B2 | 1/2008 | Blamey et al. |
| 7,382,850 | B2 | 6/2008 | Zierhofer |
| 7,822,478 | B2 | 10/2010 | Killian et al. |
| 7,917,224 | B2 | 3/2011 | Zierhofer |
| 7,921,007 | B2 * | 4/2011 | Van de Par ........... G10L 19/028 704/200.1 |
| 7,937,157 | B2 | 5/2011 | Zierhofer |

(Continued)

FOREIGN PATENT DOCUMENTS

| EP | 1742510 A2 | 1/2007 |
| KR | 10-2009-0065788 A | 6/2009 |
| WO | 02/17678 A1 | 2/2002 |

OTHER PUBLICATIONS

Blamey, et al., "An incremental excitation scale for cochlear implants," Dickson et al.: Acoustics Research Letters Online, ARLO 5(2), Apr. 2004, Published Online Mar. 1, 2004, pp. 50-55.

(Continued)

Primary Examiner — Carl H Layno
Assistant Examiner — Erin M Piateski
(74) Attorney, Agent, or Firm — Edell, Shapiro & Finnan, LLC

(57) ABSTRACT

Presented herein are excitation modeling and matching sound coding techniques that are configured to account for a recipient's estimated or predetermined neural response so as to improve a recipient's ability to perceive sound. More specifically, the techniques presented herein correlate a modeled excitation pattern with a target excitation pattern to generate a pattern of stimulation current configured to evoke an excitation pattern within the recipient's auditory system that approximates the target excitation pattern.

20 Claims, 14 Drawing Sheets

(56) References Cited

U.S. PATENT DOCUMENTS

| | | |
|---|---|---|
| 8,165,686 B2 | 4/2012 | Zierhofer |
| 8,260,429 B2 | 9/2012 | Blamey et al. |
| 8,346,368 B2 | 1/2013 | Killian |
| 8,428,742 B2 | 4/2013 | Zierhofer |
| 2007/0129772 A1 | 6/2007 | Loeb |
| 2007/0179565 A1 | 8/2007 | Overstreet et al. |
| 2009/0018615 A1* | 1/2009 | Blamey .............. A61N 1/36032 607/57 |
| 2011/0230934 A1 | 9/2011 | Zierhofer |
| 2011/0288613 A1* | 11/2011 | Smith ................ A61N 1/36032 607/57 |

OTHER PUBLICATIONS

Zierhofer, et al., "Simultaneous Intracochlear Stimulation Based on Channel Interaction Compensation: Analysis and First Results," IEEE Transactions on Biomedical Engineering, vol. 55, No. 7, Jul. 2008, pp. 1907-1916.

Kals, et al., "Results with a cochlear implant channel-picking strategy based on 'Selected Groups'," Research paper, Hearing Research, vol. 26, Feb. 2010, pp. 63-69.

Bader, et al., "Compensation for channel interaction in a simultaneous cochlear implant coding strategy," The Journal of the Acoustical Society of America, vol. 133, No. 6, Jun. 2013, pp. 4124-4132.

International Search Report and Written Opinion in counterpart International Application No. PCT/IB2015/051712, dated Jul. 15, 2015, 10 pages.

* cited by examiner

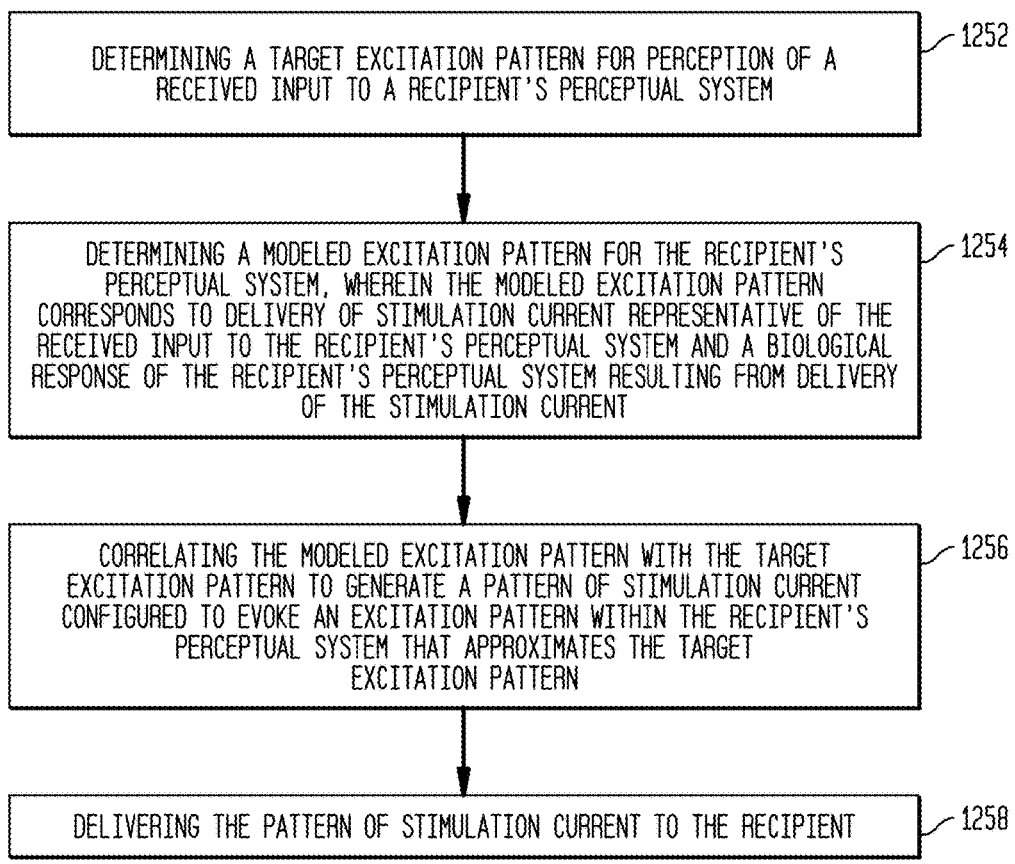

EXCITATION MODELING AND MATCHING

CLAIM OF PRIORITY

This application claims the benefit of priority under 35 U.S.C. § 119(e) of Van Dijk et al., U.S. Provisional Patent Application Ser. No. 61/950,316, entitled "Excitation Modeling and Matching", filed on Mar. 10, 2014.

BACKGROUND

Field of the Invention

The present invention relates generally to tissue-stimulating prostheses, and more particularly, to excitation modeling and matching in tissue-stimulating prostheses.

Related Art

There are several types of medical devices that operate by delivering stimulation signals (e.g., electrical signals, optical signals, etc.) to the nerves, muscle or other tissue fibers of a recipient. These medical devices, referred to herein as tissue-stimulating prostheses, typically deliver stimulation to compensate for a deficiency in the recipient. For example, tissue-stimulating hearing prostheses, such as cochlear implants, are often proposed when a recipient experiences sensorineural hearing loss due to the absence or destruction of the cochlea hair cells, which transduce acoustic signals into nerve impulses.

An auditory brainstem stimulator is another type of tissue-stimulating hearing prosthesis that may also be proposed when a recipient experiences sensorineural hearing loss due to damage to the auditory nerve. Auditory brainstem stimulators evoke a hearing percept by delivering electrical stimulation to the auditory brainstem nuclei of a recipient.

SUMMARY

In one aspect of the invention, a method is provided. The method comprises determining a target excitation pattern for perception of a received input to a recipient's perceptual system; determining a modeled excitation pattern for the recipient's perceptual system, wherein the modeled excitation pattern corresponds to delivery of stimulation current representative of the received input to the recipient's perceptual system and a biological response of the recipient's perceptual system resulting from delivery of the stimulation current; correlating the modeled excitation pattern with the target excitation pattern to generate a pattern of stimulation current configured to evoke an excitation pattern within the recipient's perceptual system that approximates the target excitation pattern; and delivering the pattern of stimulation current to the recipient.

In another aspect of the present invention, a method for stimulating a recipient's auditory system is provided. The method comprises decomposing sound received during a time frame into a plurality of frequency bands; extracting channel magnitudes from each frequency band; and executing sound coding to convert the channel magnitudes into a resulting stimulation pattern configured to evoke an excitation pattern within the recipient's auditory system that approximates a shape of a target excitation pattern. The sound coding is configured to account for a neural response to stimulation within the recipient's auditory system to generate the resulting stimulation pattern.

In a further aspect, a hearing system is provided. The hearing system comprises a sound input element configured to receive a sound signal, and a sound processor configured to generate a set of energy levels that represent the sound signal, and generate a set of modified energy levels based on an estimated or predetermined neural response of the recipient's auditory system to stimulation, wherein the set of modified energy levels is useable to evoke an excitation pattern within a recipient's auditory system that approximately matches a shape of a target excitation pattern configured to evoke perception of the sound signal by the recipient's auditory system.

BRIEF DESCRIPTION OF THE DRAWINGS

Embodiments of the present invention are described herein in conjunction with the accompanying drawings, in which:

FIG. 12 is a flowchart of a method in accordance with embodiments presented herein;

DETAILED DESCRIPTION

Presented herein are excitation modeling and matching sound coding techniques that are configured to account for a recipient's estimated or measured neural response (e.g., spread of excitation, refractory behavior, etc.) so as to improve a recipient's ability to perceive sound. More specifically, the techniques presented herein correlate a modeled excitation pattern with a target excitation pattern to generate a pattern of stimulation current configured to evoke an excitation pattern within the recipient's auditory system that approximates the shape of the target excitation pattern.

For ease of illustration, the excitation modeling and matching techniques are primarily described herein with reference to one type of tissue-stimulating prosthesis, namely a cochlear implant. However, it is to be appreciated that the techniques presented herein may be used with other tissue-stimulating prosthesis including, for example, auditory brainstem stimulators, implantable pacemakers, defibrillators, functional electrical stimulation devices, pain relief stimulators, visual prostheses, other neural or neuromuscular stimulators, etc.

Figure 1:
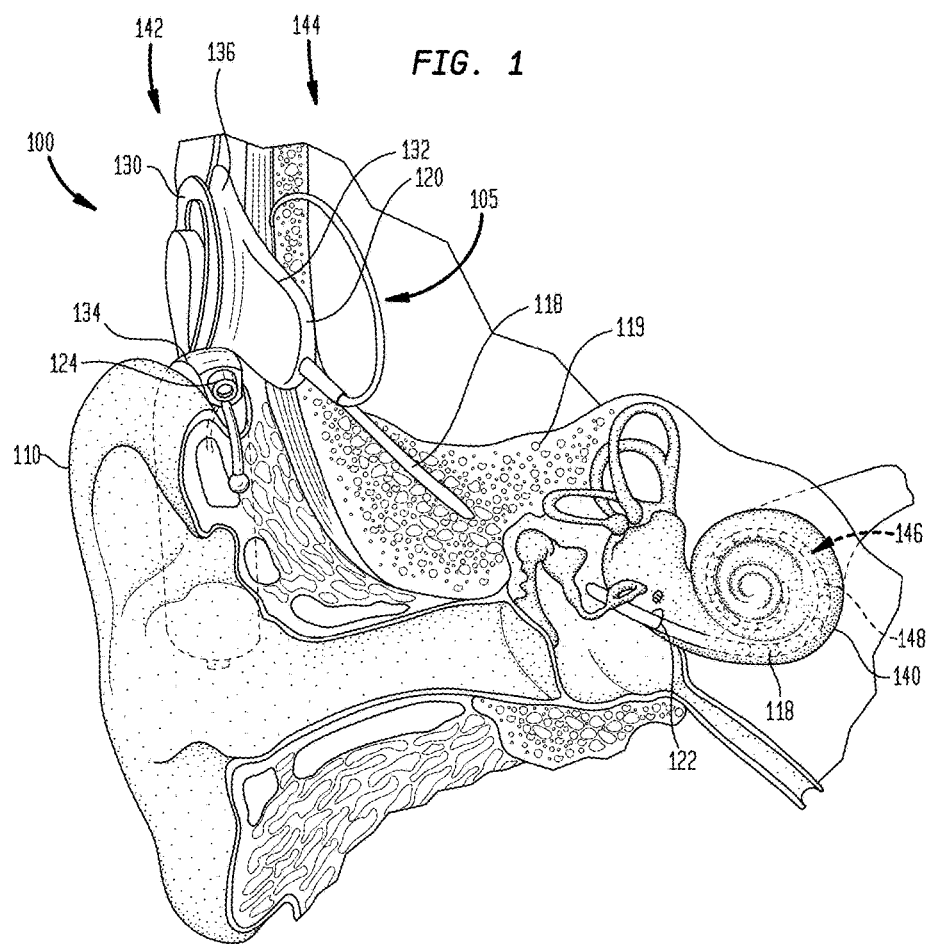
FIG. 1 is a schematic diagram of a cochlear implant configured to perform excitation modeling and matching in accordance with embodiments presented herein.

FIG. 1 is perspective view of an exemplary cochlear implant 100 configured to execute excitation modeling and matching techniques in accordance with embodiments presented herein. The cochlear implant 100 includes an external component 142 and an internal or implantable component 144. The external component 142 is directly or indirectly attached to the body of the recipient and typically comprises an external coil 130 and, generally, a magnet (not shown in FIG. 1) fixed relative to the external coil 130, one or more sound input elements 124 (e.g., microphones, telecoils, etc.) for detecting sound and a sound processing unit 134. The sound processing unit 134 may include, for example, a power source (not shown in FIG. 1) and a sound processor (also not shown in FIG. 1). The sound processor is configured to process electrical signals generated by a sound input element 124 that is positioned, in the depicted embodiment, by auricle 110 of the recipient. The sound processor provides the processed signals to external coil 130 via a cable (not shown in FIG. 1).

FIG. 1 illustrates an example in which cochlear implant 100 includes an external component 142 with an external sound processor. It is to be appreciated that the use of an external component is merely illustrative and that the techniques presented herein may be used in arrangements having an implanted sound processor (e.g., totally implantable cochlear implants). It is also to be appreciated that the individual components referenced herein, e.g., sound input element 124 and the sound processor in sound processing unit 134, may be distributed across more than one tissue-stimulating prosthesis, e.g., two cochlear implants 100, and indeed across more than one type of device, e.g., cochlear implant 100 and a consumer electronic device or a remote control of the cochlear implant 100.

The implantable component 144 comprises an implant body 105, a lead region 108, and an elongate stimulating assembly 118. The implant body 105 comprises a stimulator unit 120, an internal coil 136, and an internal receiver/transceiver unit 132, sometimes referred to herein as transceiver unit 132. The transceiver unit 132 is connected to the internal coil 136 and, generally, a magnet (not shown) fixed relative to the internal coil 136. Internal transceiver unit 132 and stimulator unit 120 are sometimes collectively referred to herein as a stimulator/transceiver unit 120.

The magnets in the external component 142 and implantable component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is at least partially implanted in cochlea 140 and includes a contact array 146 comprising a plurality of stimulating contacts 148. Contact array 146 may comprise electrical contacts and/or optical contacts. For ease of illustration, the excitation modeling techniques are described with reference to electrical contacts and the delivery of electrical stimulation signals to a recipient.

Stimulating assembly 118 extends through cochleostomy 122 and has a proximal end connected to stimulator unit 120 via lead region 108 that extends through mastoid bone 119. Lead region 108 couples the stimulating assembly 118 to implant body 105 and, more particularly, stimulator/transceiver unit 120.

In general, the sound processor in sound processing unit 134 is configured to execute sound coding to convert a detected sound into a coded signal corresponding to electrical signals for delivery to the recipient. The coded signal generated by the sound processor is then sent to the stimulator/transceiver unit 120 via the RF link between the external coil 130 and the internal coil 136. The stimulator/transceiver unit 120 includes a circuit that processes the received coded signal and outputs a series of stimulation signals via one or more stimulation channels that terminate in the stimulating contacts 148. As such, the stimulation signals are delivered to the recipient via the stimulating contacts 148. In this way, cochlear implant 100 stimulates the recipient's auditory nerve cells, bypassing absent or defective hair cells that normally transduce acoustic vibrations into neural activity.

As noted, a primary purpose of cochlear implant sound coding is to map received sounds into a series of electrical current pulses/signals, referred to herein as a stimulation pattern, to be delivered via stimulation channels terminating in electrical contacts implanted in the cochlea. An important aspect of sound coding is how to preserve the intelligibility and quality of target sounds both in quiet and adverse (e.g., noisy) listening environments. As such, different sound coding algorithms have been developed to mimic the firing patterns inside the cochlea as closely as possible.

A sound coding algorithm may determine, for example, the amplitude, the width, the shape, the timing, and the stimulation channel (place/contact) of a current signal. To mimic the tonotopic organization of the cochlea, sound coding algorithms typically decompose the input sound signal into different frequency bands using a filter bank. The algorithm then extracts envelope amplitude information, sometimes referred to herein as a channel magnitude, in each frequency band. These channel magnitudes are then used to determine the level of stimulation current delivered via a corresponding stimulation channel. Thus, the filter bank emulates the behavior of the cochlea in a normal ear, where different locations along the length of cochlea are sensitive to different frequencies. The number of channel magnitudes (envelopes) and stimulation channels selected for use in stimulating the recipient at each cycle differs for different strategies.

The delivery of a stimulation pattern (i.e. a pattern of stimulation signals/current pulses) to a recipient's cochlea results in an excitation pattern within the cochlear nerve. As used herein, an excitation pattern is a neural response produced within the recipient's tissue (e.g., auditory system, including cochlear nerve, auditory nerve, brainstem, etc.) in response to the delivery of stimulation signals. Stimulation signals delivered via different stimulation channels are intended to stimulate independent populations of neurons within the cochlea. In practice, however, when stimulation signals are delivered via an electrical contact of a stimulation channel, the stimulation may spread from the electrical contact so as to excite neurons not only near the electrical contact, but also at various distances from the electrical contact. This phenomenon is known as spread of excitation (SOE) and can affect the effectiveness of a delivered stimulation pattern. Spread of excitation may disturb the place pitch percept as well as cause temporal information to be spread across channels. That is, due to the overlapping stimulus regions, any given neuron will generally be driven by pulses from multiple channels, thereby receiving the combination of multiple stimulation patterns rather than just one stimulation pattern as desired. With respect to the examples presented herein, a "pattern" or "shape" refers to a profile produced by plotting stimulation magnitudes at corresponding stimulation channels.

Figure 2:
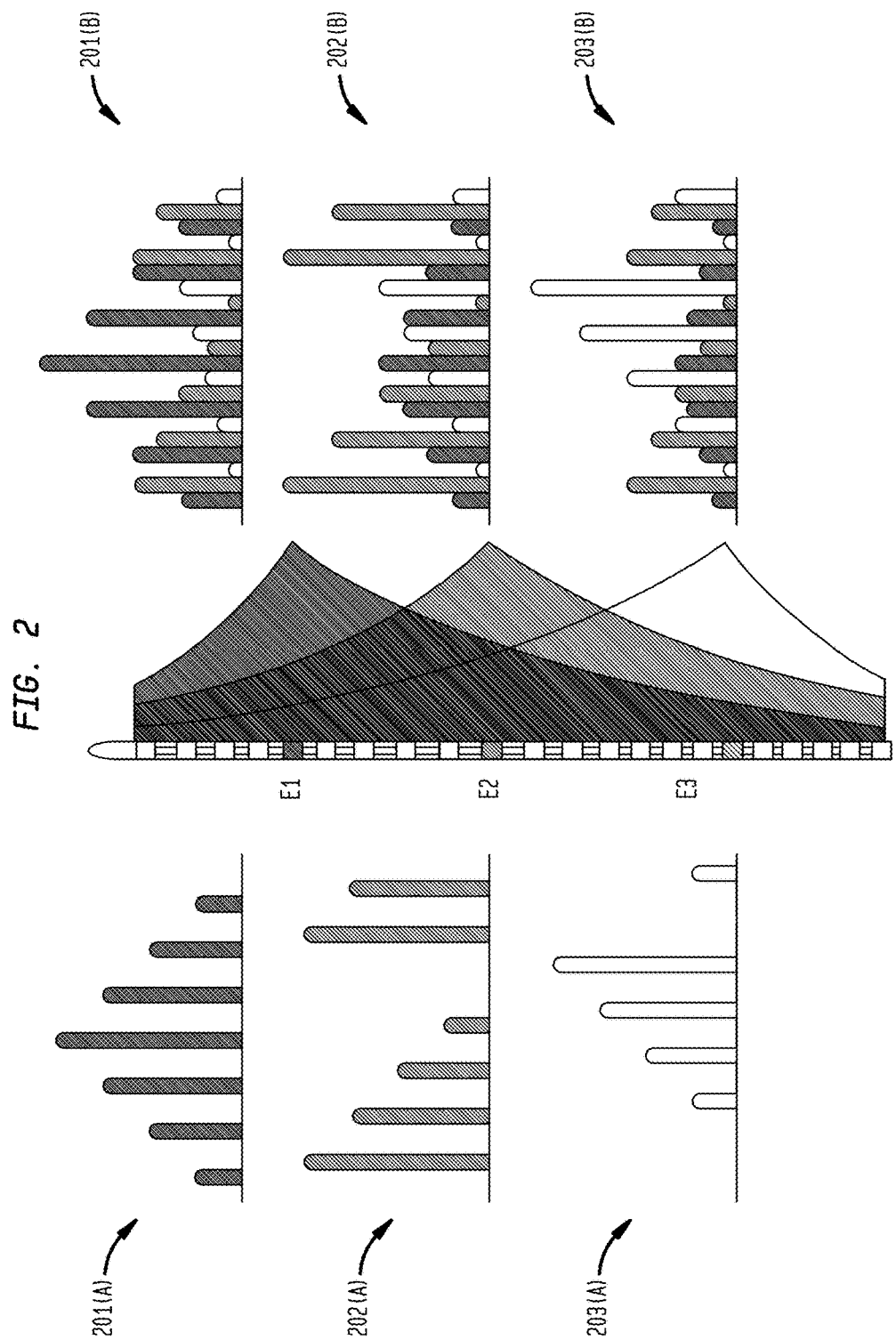
FIG. 2 is a schematic diagram illustrating the effects of excitation spread within a recipient's cochlea.

For example, FIG. 2 is a schematic diagram illustrating how the spread of excitation disturbs temporal information. FIG. 2 illustrates temporal information 201(A), 202(A), and 203(B) extracted from a first channel (E1), a second channel (E2), and a third channel (E3), respectively. Due to the spread of excitation, the temporal information 201(A), 202(A), and 203(A) mixes together such that part of the temporal information of the various individual channels will also appear at the locations of the other channels. FIG. 2 illustrates the temporal information 201(B), 202(B), and 203(B) present on each of the channels 1, 2, and 3 as result of the spread of excitation.

Advanced Combinational Encoder (ACE) and Continuous Interleaved Sampling (CIS) are strategies used in current cochlear implants. The ACE strategy is based on the so-called "N of M" principle wherein a received signal is processed in a number of frequency bands (i.e., M bands) for each analysis frame of recorded sound. After envelope detection and extraction of the channel magnitudes, the N frequency bands containing the largest magnitudes (i.e., largest amplitude envelopes) are selected for use in delivering stimulation. The basic aim of the ACE strategy is to neglect the less significant spectral components and to concentrate on the more significant spectral features. In contrast, the CIS strategy identifies a fixed number of channel magnitudes and all corresponding stimulation channels are used for stimulation in every analysis frame. Due at least in part to spread of excitation, the ACE and CIS strategies may not generate a stimulation pattern that is able to evoke an excitation pattern that best represents the received sound.

Figure 3:
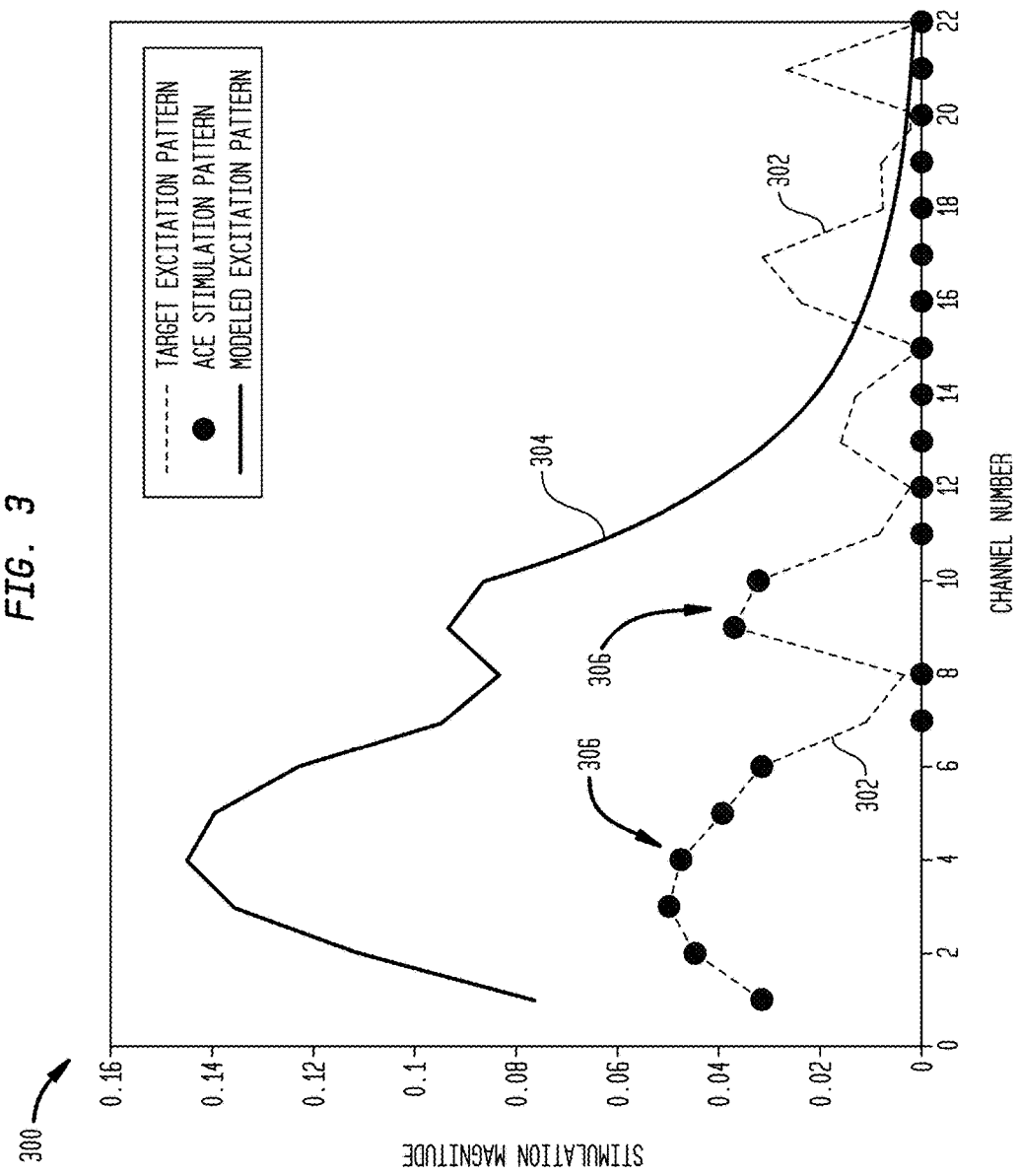
FIG. 3 is a graph illustrating a target excitation pattern and a modeled excitation pattern corresponding to an Advanced Combinational Encoder stimulation pattern.

More specifically, FIG. 3 is a graph 300 illustrating a target excitation pattern 302, a modeled excitation pattern 304, and an ACE stimulation pattern 306. The target excitation pattern 302 is a desired neural response that would, ideally, result in substantially complete perception of a received sound within an analysis frame. The target excitation pattern 302 is generated from the spectral information present in a plurality of frequency bands representing the received sound.

FIG. 3 illustrates an example where a subset of twenty-two (22) total channels is used to deliver an ACE stimulation pattern 306. In the ACE stimulation pattern 306, the eight (8) (i.e., N=8) frequency bands containing the largest channel magnitudes are detected and used for stimulation. The eight largest channel magnitudes are detected at channels 1, 2, 3, 4, 5, 6, 9 and 10. Therefore, stimulation signals are delivered only at these eight channels and no stimulation signals are delivered at the remaining fourteen channels. In the example of FIG. 3, the ACE stimulation pattern 306 tracks the target excitation 302 only where the largest channel magnitudes are detected. However, at channels with smaller detected magnitudes (e.g., channels 16-22) spectral information is not properly represented. In other words, the recipient would not be able to perceive the information in the higher frequency bands.

As noted, FIG. 3 also illustrates a modeled excitation pattern 304. The modeled excitation pattern 304 is a calculated combination of the ACE stimulation signals (delivered stimulation current), the recipient's neural response to those ACE stimulation signals, as well as the recipient's neural response to previously delivered ACE stimulation signals. In other words, the modeled excitation pattern 304 accounts for the recipient's estimated or predetermined neural response, including the spread of excitation and refractory behavior, to a delivered stimulation pattern. Further details are provided below regarding the generation of a modeled excitation pattern to account for an estimated or predetermined neural response in accordance with embodiments presented herein.

In the example of FIG. 3, the modeled excitation pattern 304 represents the excitation pattern likely to be evoked in response to delivery of the ACE stimulation pattern 306. In the cochlea region associated with the stimulated channels (i.e., channels 2-6, 9, and 10), the stimulation magnitudes of the modeled excitation 304 are significantly higher than both the target excitation pattern 302 and the ACE stimulation pattern 306. This is due to, for example, the spread of excitation resulting from the delivery of the stimulation signals at those channels, refractory behavior, etc. Additionally, due to the fact that no stimulation signals are delivered at channels 11-22, several peaks of the target excitation pattern 302 are not captured in the modeled excitation pattern 304. Due to the increased stimulation magnitudes and the non-captured peaks, when the ACE stimulation 306 is delivered to the recipient, the recipient may not correctly perceive the received sound.

The excitation modeling and matching techniques presented herein are configured to perform sound coding in a manner that accounts for a recipient's estimated or predetermined neural response (e.g., spread of excitation, refractory behavior, etc.) and improve a recipient's ability to perceive sound. Notably, the techniques presented herein attempt to maximize correlation between the modeled and target excitation patterns rather than attempt to minimize the error between the patterns. In this way, the excitation modeling techniques can generate a stimulation pattern configured to evoke an excitation pattern having a shape, when plotted as shown in FIG. 3, that approximately matches the shape of the target excitation pattern without taking into account the overall stimulation level, which is not possible with error minimization techniques. In particular, correlation maximization is able to preserve the relative strength of speech formants, whereas minimizing error does not preserve this relationship.

Figure 4:
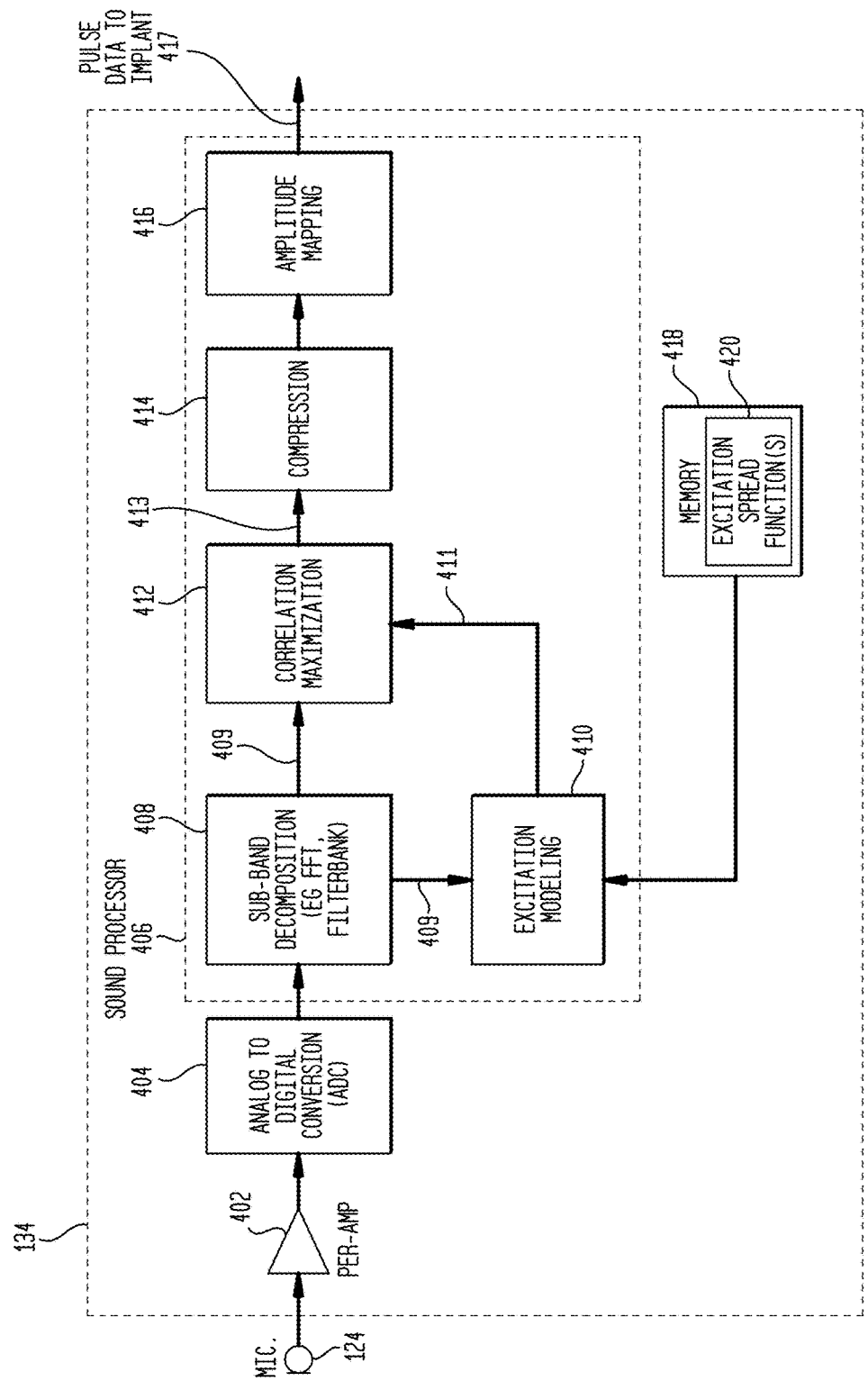
FIG. 4 is a functional block diagram of a sound processing unit in accordance with embodiments presented herein.

FIG. 4 is a functional block diagram of one embodiment of a portion of the sound processing unit 134 in accordance with embodiments presented herein. As noted above, sound processing unit 134 comprises one or more sound input elements 124 that are configured to receive a sound (audio signal). In the example of FIG. 4, the one or more sound input elements 124 comprise a single microphone 124 that converts an acoustic signal to an electrical signal.

The sound processing unit 134 also comprises a pre-amplifier 402 that receives the electrical signal generated by the microphone and an analog-to-digital converter (ADC)

404. The pre-amplifier 402 may include an Automatic Gain Control (AGC) to amplify and control the level of the electrical signal generated by the microphone 124. The ADC 404 is configured to convert the electrical signal to a stream of digital samples for processing by the remaining components of the sound processing unit 134.

As shown by the dashed box in FIG. 4, the remaining elements of sound processing unit 134 may be implemented as part of a sound processor 406. In certain embodiments, the sound processor 406 may be a digital signal processor (DSP). Alternatively, the sound processor 406 may be implemented in one or more application-specific integrated circuits (ASICs), other hardware, or a combination of hardware and software, as deemed appropriate for the particular application. Sound processor 406 first comprises a sub-band decomposition block 408 configured to separate (e.g., using a Fast Fourier Transform (FFT) Filter bank) the digitized audio signal into a plurality of frequency bands. The sub-band decomposition block 408 may also be configured to perform amplitude envelope (channel magnitude) extraction/detection. The output of sub-band decomposition module 408 may be, at a given time instance, a plurality channel magnitudes 409 across a range of frequency bands.

The channel magnitudes 409 are provided to an excitation modeling block 410 and a correlation maximization block 412. The excitation modeling block 410 is configured to use the amplitude envelopes to generate a modeled excitation pattern 411 that is provided to correlation maximization block 412. As described in detail below, the modeled excitation pattern 411 is a model or estimate of an excitation pattern that is likely to be evoked when a selected stimulation pattern generated from the channel magnitudes 409 is delivered to a recipient. Also as described further below, the excitation modeling block 410 generates the modeled excitation pattern 411 by taking into account the neural response of the recipient's cochlea. For example, the excitation modeling block 410 may take into account spread of excitation, refractory behavior, dead zones, etc. that all form part of a neural response to a delivered stimulation pattern.

As shown, the sound processing unit 134 includes a memory 418 comprising one or more excitation spread functions 420 for the stimulation channels of the cochlear implant. The excitation spread function(s) 420 characterize a recipient's neural response to stimulation (e.g., how stimulation signals delivered via stimulation channels will affect other stimulation channels). The excitation spread function(s) 420 are provided to the excitation modeling block 410 for use in generating the modeled excitation pattern 411. As described further below, the excitation spread function(s) 420 may be a predetermined recipient-specific excitation spread function(s) or may be estimated linear and symmetric spread function(s).

As noted, the modeled excitation pattern 411 is provided to the correlation maximization block 412. In general, the correlation maximization block 412 is configured to correlate the modeled excitation pattern 411 with a target excitation pattern corresponding to the channel magnitudes 409 so as to generate a set of channel magnitudes that, when converted to current signals for delivery to the recipient, will evoke an excitation pattern having a shape that approximately matches the shape of target excitation pattern. In other words, correlation maximization block 412 is configured to modify the channel magnitudes 409 in a manner that maximizes the correlation between the modeled excitation pattern 411 and the target excitation pattern. The correlation maximization block 412 generates modified channel magnitudes 413 that are then compressed at compression block 414 and mapped to patient specific current levels at amplitude mapping block 416. The compressed and mapped modified channel magnitudes 417 are then provided to the implantable component for use in generating stimulation signals for delivery to the recipient.

As noted, the excitation modeling block 410 is configured to use the channel magnitudes 409 to generate the modeled excitation pattern 411 using one or more excitation spread function(s). That is, a physiological spread function for each stimulation channel and terminating electrical contact may be used to model an excitation pattern in the cochlea in response to electrical stimulation signals. In certain embodiments, an excitation spread function for m number of electrodes/channels can be represented by a matrix, referred to herein as an excitation spread matrix or SOE matrix given as:

$$SOE = \begin{pmatrix} s11 & s12 & s13 & \ldots & s1m \\ s21 & s22 & s31 & \ldots & s2m \\ s31 & s32 & s33 & \ldots & s3m \\ \ldots & \ldots & \ldots & \ldots & \ldots \\ sm1 & \ldots & \ldots & \ldots & smm \end{pmatrix}$$

where a coefficient $s_{cb}$ represents the excitation present on a channel b due to the stimulation on another channel c.

An excitation spread matrix may be developed through the use of several different techniques. In one embodiment, the excitation spread matrix may be a predetermined recipient-specific excitation spread matrix determined through a fitting procedure. For example, a fitting procedure could be conducted where electrical current is delivered via a first stimulation channel. Forward masking and/or neural response telemetry (NRT) could then be used to measure how much the electrical current delivered at the first stimulation channel affects each of the other stimulation channels (i.e., determine how the electrical current from the first channel stimulates neurons at the other stimulation channels). This process can be repeated for the other channels to generate a complete excitation spread matrix that is stored for subsequent use.

In other embodiments, the excitation spread matrix can represent an estimated excitation spread. For example, it could be assumed that a spread function shows approximately exponential decays in all electrodes whereby the slopes toward the apex are shallower than towards the base. As such, an excitation spread matrix could be generated in accordance with such attributes. In a simpler embodiment, a linear and symmetric excitation spread matrix with a set overlap (e.g., where $\xi=0.5$ indicating a 50% overlap) between the adjacent channels which decreases exponentially on the neighboring channels. An example symmetric and linear SOE matrix with m channels and an overlap ($\xi$) between the adjacent channels is shown below. The excitation on any one channel is due to the combined effect of m channels and excitation spread decreases exponentially on the neighboring channels.

$$SOE = \begin{pmatrix} 1 & \xi & \xi & \ldots & \xi^m \\ \xi & 1 & \xi & \ldots & \xi^{m-1} \\ \xi^2 & \xi & 1 & \ldots & \xi^{m-1} \\ \ldots & \ldots & \ldots & \ldots & \ldots \\ \xi^m & \ldots & \ldots & \ldots & 1 \end{pmatrix}$$

When a number of channels are stimulated simultaneously, the effective stimulation is due to the combined effect of all the channels being stimulated. Thus, the stimulation pattern in the cochlea can be modeled as a linear combination of all the stimulation channels and the excitation spread functions. Another factor that can be taken into account is the refractory properties (behavior) of the stimulated neural populations. More specifically, the stimulated neurons have a refractory behavior that momentarily prevents the neural population from reacting to subsequent pulses that occur in quick succession. This can be modeled as a residual excitation from the previous time frame. Assuming that E is a vector of the channel magnitudes (amplitude envelopes) which are later mapped into current levels based on the recipient's electrical dynamic range, then for simultaneous stimulation the modeled effective envelope amplitudes at a given time instance ($EE_t$) that will be excited after the SOE can be given as shown below in Equation 1.

$$EE_t = SOE \times E_t + \alpha \times EE_{(t-1)}.$$  Equation 1:

where SOE is the excitation spread matrix, Et is a vector of the envelope magnitudes, $EE_{(t-1)}$ is the attenuated effective envelopes from the previous analysis frame, and a is an attenuation constant.

The refractory behavior of the neural response is taken into account by introducing the attenuated effective envelopes ($EE_{(t-1)}$) from the previous analysis frame. The attenuation constant ($\alpha$) may depend upon the recovery function and the rate of stimulation.

For a non-simultaneous stimulation embodiment, the stimulation on a channel x can only influence the excitation on channel y if channel x is stimulated before channel y. However, the stimulation on channel y cannot influence the stimulation on channel x in the current analysis frame since channel x has been stimulated before channel y. Therefore, the influence of stimulation delivered via channel y will be taken into account in the next analysis frame. Thus, the excitation spread matrix can be divided into a lower and an upper triangular matrix to take into account the order of stimulation. Equation 2, shown below, models the spread of excitation and the refractory behavior of the neural response for non-simultaneous stimulation embodiments.

$$EE_t = SOE1 \times E_t + SOE2 \times E_{(t-1)} + \alpha \times EE_{(t-1)}$$ Equation 2:

where SOE1 is a lower triangular matrix, SOE2 is a strictly upper triangular matrix, Et is a vector of the envelope magnitudes, $EE_{(t-1)}$ is the attenuated effective envelopes from the previous analysis frame, and $\alpha$ is an attenuation constant.

In certain examples, sound signals are short time stationary. Therefore, at sufficiently high stimulation rates, Equation 2 can be approximated by Equation 1.

Figure 5:
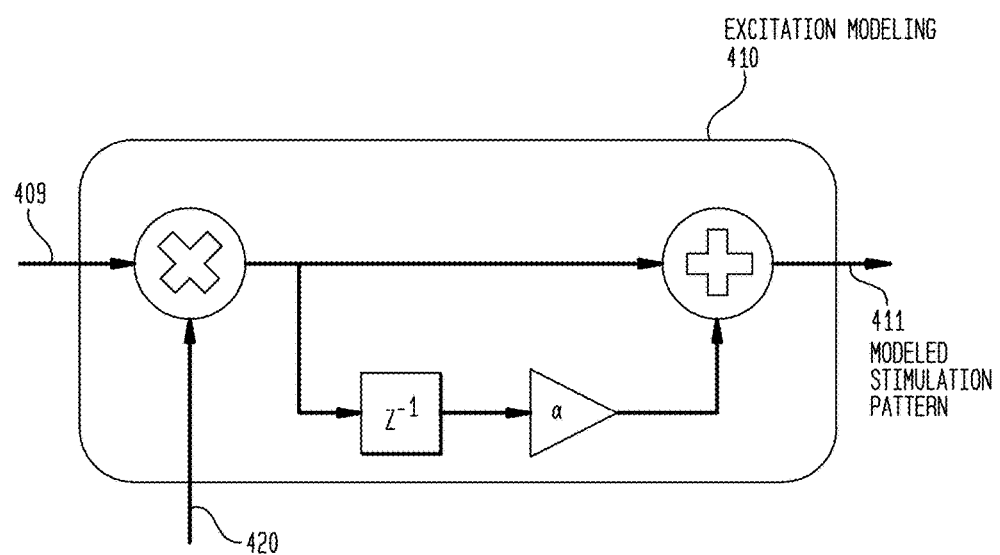
FIG. 5 is a functional block diagram of an excitation modeling block of a sound processing unit in accordance with embodiments presented herein.

FIG. 5 is a functional block diagram illustrating the above operations of the excitation modeling block 410 for a non-simultaneous stimulation embodiment. As shown, the channel magnitudes 409 (i.e., $E_t$) and the excitation spread function(s) 420 (e.g., an excitation spread matrix SOE) are received and combined with one another by the excitation modeling block 410 (i.e., SOE×$E_t$). This combination is then added to a combination of the channel magnitudes from a previous analysis frame (i.e., $EE_{(t-1)}$) and the attenuation constant ($\alpha$).

A cochlear implant recipient's ability to correctly perceive sound is related to the ability to perceive spectral shapes (among other things). As shown in FIG. 3 above, the relative strength of different speech formants is not always preserved in the ACE generated modeled excitation pattern due to the combined effect of maxima selection and the resulting neural response (e.g., excitation spread). That is, the ACE maxima selection does not offer an optimum solution that preserves the shape of the target stimulation pattern within the modeled pattern. The excitation modeling and matching techniques presented herein are configured to preserve the shape of the target (desired) excitation and therefore the relative strength of different speech formants after, e.g., the SOE is taken into account. As such, the excitation modeling and matching techniques may not only improve the speech intelligibility in noise, but can also be less dependent upon the frequency response of the channel. This is especially true for non-symmetric and non-equal spread functions across the electrode array. These and other objectives are achieved by the correlation maximization block 412.

More particularly, the correlation maximization block 412 is configured to preserve the shape of the target stimulation pattern by modifying the channel envelopes (and thus the resulting stimulation pattern) such that correlation between the target excitation pattern and the modeled excitation pattern is maximized. A cost function for maximizing this correlation can be given as shown below in Equation 3.

$$J(W) = Corr\{E_t, SOE \times (E_t \cdot W) + \alpha \times EE_{(t-1)}\}$$ Equation 3:

where $0 \leq W \leq 1$

In certain embodiments, the cost function J(W) is maximized using a Pearson correlation to obtain values for a channels weights vector (W). That is, W is a vector of channel weights for application to the channel magnitudes that, when properly selected, maximize the correlation between the target excitation pattern and the modeled excitation pattern. In this example, the values in the channel weights vector can have a value between 0 and 1. After solving the cost function, the selected values in the channels weights vector (weighting factors) can be used to adjust/modify the channel magnitudes for use in delivering stimulation to the recipient.

Figure 6:
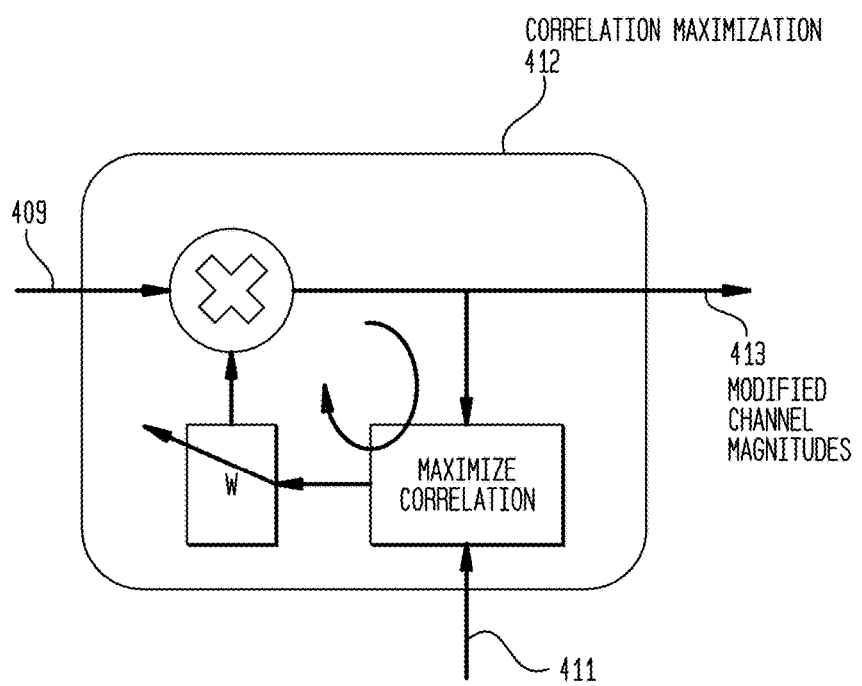
FIG. 6 is a functional block diagram of a correlation maximization block of a sound processing unit in accordance with embodiments presented herein.

FIG. 6 is a functional block diagram illustrating the operation of correlation maximization block 412 in accordance with Equation 3. FIG. 6 illustrates the iterative process to change the values of the channel weights vector to maximize the Pearson correlation between the target and modeled excitation patterns.

The cost function shown in Equation 3 is a constrained combinatorial optimization problem and can be solved using, for example, the gradient ascent method, a steepest ascent method, or any other algorithm. An updated equation for the channel weights vector can be given as shown below in Equation 4.

$$W_{j+1} = W_j - \rho\left(\frac{\partial J(W)}{\partial W}\right)$$ Equation 4

In one example, the channel weights vector is initialized with a unity gain for all channels and then the weights are adapted in each iteration (j) sequentially for all the channels to maximize the cost function J(W). As detailed further, several iterations may be necessary to obtain the global maxima for $0 \leq W \leq 1$.

Figure 7:
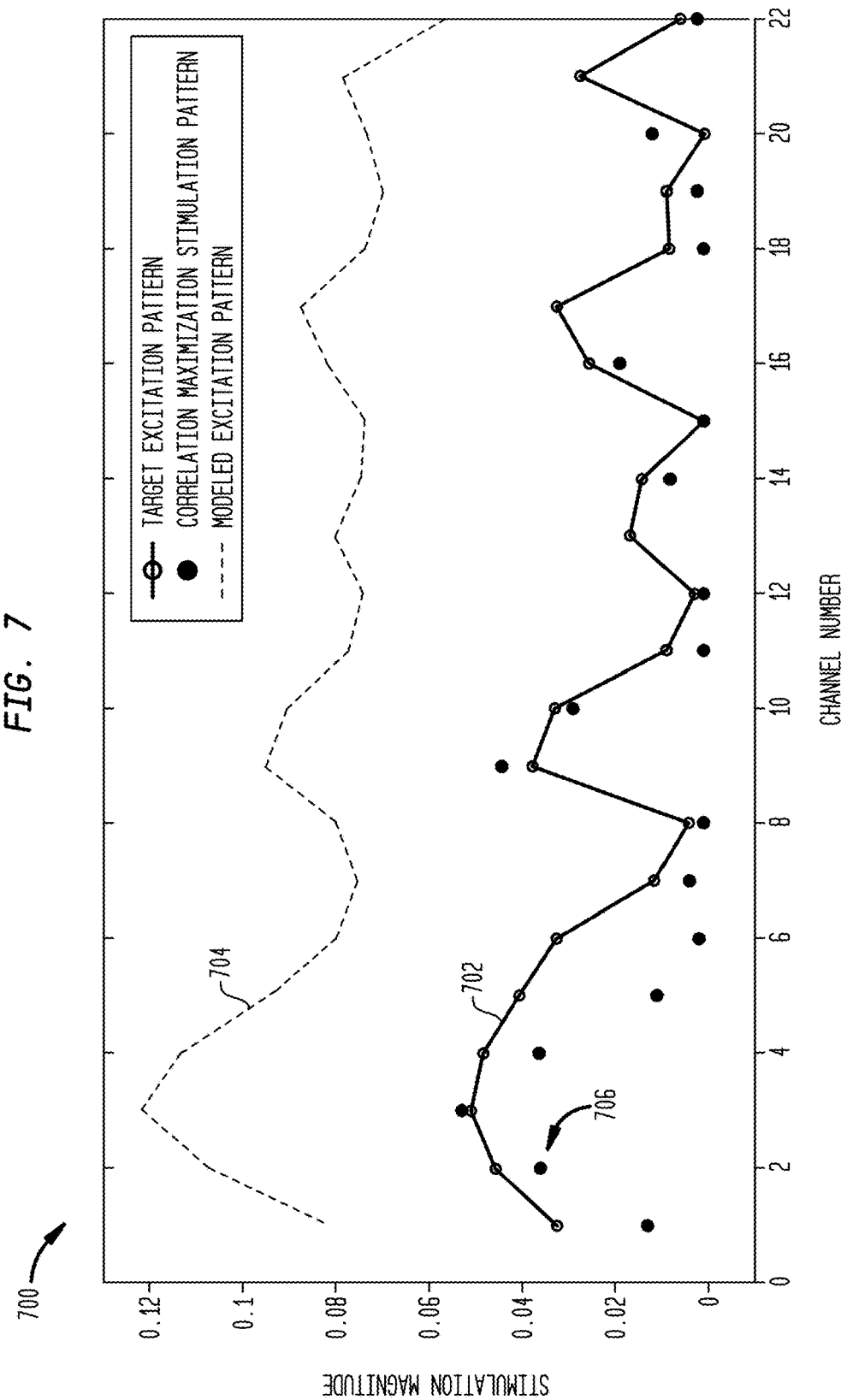
FIG. 7 is a graph illustrating a modeled excitation pattern that is correlated to a target excitation pattern in accordance with embodiments presented herein.

FIG. 7 is a graph 700 illustrating a target excitation pattern 702, a modeled excitation pattern 704, and a resulting stimulation pattern 706 determined through the correlation maximization techniques of Equation 3. The resulting stimulation pattern 706 is sometimes referred to herein as a correlation maximization stimulation pattern. As shown, the target excitation pattern 702, modeled excitation pattern 704, and the correlation maximization stimulation pattern 706 are represented in FIG. 7 as plots of stimulation magnitudes at corresponding stimulation channels.

By maximizing the cost function of Equation 3, channel magnitudes representing a received sound are modified to generate the correlation maximization stimulation pattern 706. In this way, the correlation maximization stimulation pattern 706, when delivered to the recipient's auditory system, evokes an excitation pattern (represented by modeled excitation pattern 704) having a shape that approximately matches the shape of the target excitation pattern 702. For example, as shown in FIG. 7, the modeled excitation pattern 704 includes peaks and valleys at substantially the same locations as in the target excitation pattern 702, thereby substantially retaining the spectral information present in the target excitation pattern.

The above embodiment of Equation 3 results in the selection of all of the channels (i.e., all m channels) for use in delivering stimulation signals. However, the techniques presented herein can also be used for channel selection (i.e., selection of a subset n of the total m channels) by modifying the constraints of Equation 3. In these examples, only a number (n) of channels for which delivery of stimulation at the channel will improve correlation between the desired ($E_t$) and the modeled stimulation ($EE_t$) are selected. The cost function for maximizing correlation in these channel selection embodiments can be given as shown below in Equation 5.

Equation 5:

$$J(W)=Corr\{E_p SOE \times (E_t \cdot W) + \alpha \times EE_{(t-1)}\} \qquad (10)$$

where, $W \in \{0, 1\}$, $\Sigma W = n$.

This cost function $J(W)$ is again maximized by adjusting the values in the channel weights vector. However, in the embodiment of Equation 5, the values in the channel weights vector can have a value of only zero (0) or one (1) and are strictly limited to n channels. In this way, the channel weights vector represents the channel selection in a binary manner where a 1 indicates that the corresponding channel is selected while a 0 indicates that the channel is not selected. In total, only the n out of the total m channels are selected for stimulation which will maximize the correlation.

To obtain an optimal solution, the correlation for all possible combinations would be calculated $$\left(\text{i.e., } \frac{m!}{(m-n)!n!}\right)$$

simultaneously. Since such a solution is difficult to implement in a real-time system, a complexity reduction may be applied where one channel at a time is selected out of the m channels which will maximize the correlation. This process may be iterated until the required (n) number of channels is selected.

In accordance with embodiments presented herein, the number (n) of selected channels is limited with a specific analysis frame. However, the number of selected channels can change from one analysis frame to the next. That is, a different number of channels can be selected in successive frames to represent the sound received at the corresponding time instance (e.g., select eight channels in a first frame, select six channels in the subsequent frame, and so on).

As noted above, in accordance with Equation 3, the maximum channel magnitudes are not necessarily stimulated. Therefore, since some low magnitude channels may be selected in place of higher magnitude channels, some power/battery saving may be achieved. In certain implant arrangements, this may provide, for example, approximately 5% power savings (for low spread functions) to approximately 15% power savings (for higher spread functions).

Figure 8:
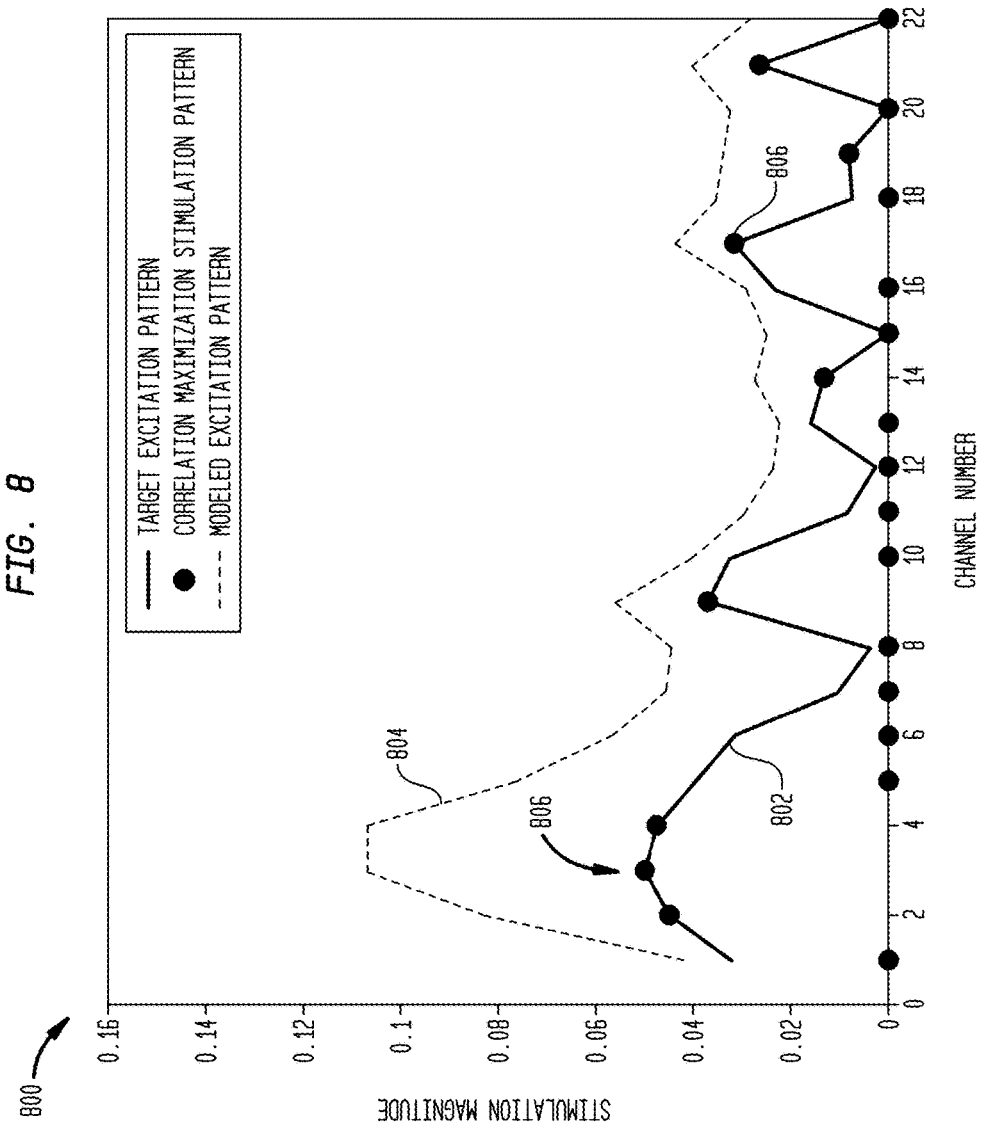
FIG. 8 is a graph illustrating another modeled excitation pattern that is correlated to a target excitation pattern in accordance with embodiments presented herein.

FIG. 8 is a graph 800 illustrating a target excitation pattern 802, a modeled excitation pattern 804, and a resulting stimulation pattern (correlation maximization stimulation pattern) 806 determined through the correlation maximization techniques of Equation 5. The target excitation pattern 802, modeled excitation pattern 804, and the correlation maximization stimulation pattern 806 are represented in FIG. 8 as plots of stimulation magnitudes at corresponding stimulation channels.

In the example of FIG. 8, twenty-two (22) stimulation channels are available (i.e., m=22). However, since the values of the channel weights vector are limited to either 0 or 1 and represent a binary selection, stimulation is only delivered via eight (8) electrodes (i.e., n=8). As shown, by maximizing the cost function of Equation 5, channel magnitudes representing a received sound are either selected or not selected to generate the correlation maximization stimulation pattern 806. In this way, the correlation maximization stimulation pattern 806, when delivered to the recipient's auditory system, evokes an excitation pattern (represented by modeled excitation pattern 804) having a shape that approximately matches the shape of the target excitation pattern 802 (i.e., substantially retains the spectral information present in the target excitation pattern).

In certain circumstances, a tissue-stimulating prosthesis may have the ability to simultaneously deliver both positive and negative stimulation currents. Equation 3 may be modified, as shown below in Equation 6, to take advantage of such abilities of the cochlear implant.

$$J(W)=Corr\{E_p SOE \times (E_t \cdot W) + \alpha \times EE_{(t-1)}\} \qquad \text{Equation 6}$$

where W is a real number i.e $W \in R$.

In Equation 6 the values of the channel weights vector can have a value between negative one (−1) and one (1). As such, the channel magnitudes may be multiplied by weights between −1 and 1. By removing the constraint of positive magnitudes, a substantially ideal resulting stimulation pattern in which the modeled excitation pattern is fully correlated with the desired excitation pattern may be possible. However, as noted, these examples rely on the ability to deliver positive and negative currents at the same time.

Figure 9:
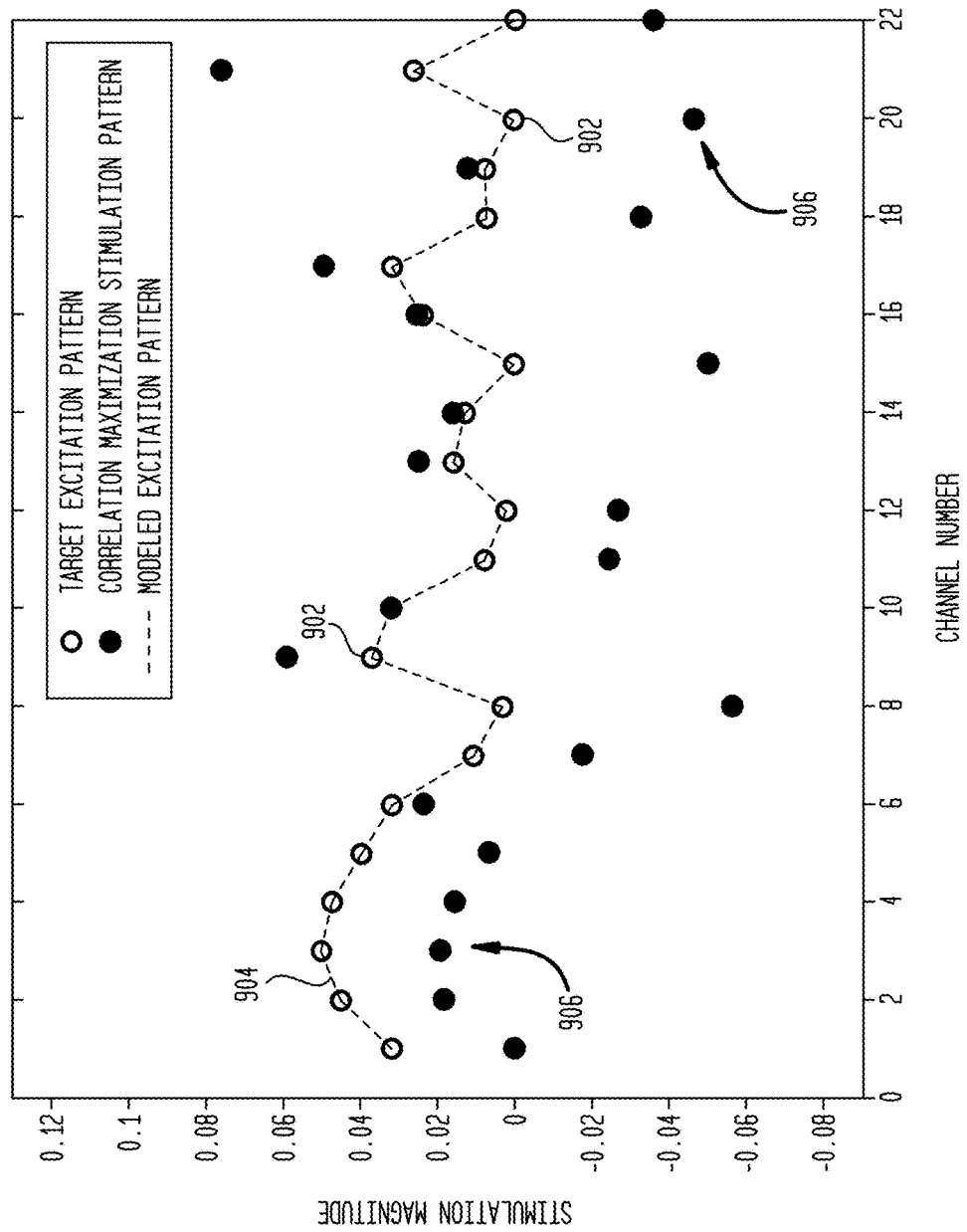
FIG. 9 is a graph illustrating a further modeled excitation pattern that is correlated to a target excitation pattern in accordance with embodiments presented herein.

FIG. 9 is a graph 900 illustrating a target excitation pattern 902, a modeled excitation pattern 904, and a resulting stimulation pattern (correlation maximization stimulation pattern) 906 determined through the correlation maximization techniques of Equation 6. The target excitation pattern 902, modeled excitation pattern 904, and the correlation maximization stimulation pattern 906 are represented in FIG. 9 as plots of stimulation magnitudes at corresponding stimulation channels.

In the example of FIG. 9, the cochlear implant has the ability to simultaneously deliver positive and negative currents at any weighting value between −1 and 1. Therefore, the cost function of Equation 6 can be maximized to select channel magnitudes that result in a correlation maximization stimulation pattern 906 that evokes an excitation pattern (represented by modeled excitation pattern 904) having a shape that exactly matches the shape of the target excitation pattern 902 (i.e., precisely retains the spectral information present in the target excitation pattern).

To reduce the computational cost associated with Equation 6, channel selection can also be applied in examples having the ability to deliver positive and negative currents at the same time. Such an example is shown below in Equation 7.

$$J(W) = Corr\{E_t SOE \times (E_t \cdot W) + \alpha \times EE_{(t-1)}\}$$ Equation 7:

where W={1, 0, −1}.

In Equation 7, the values in the channel weighting vector may be either 1, 0, or −1. This reduces the computational cost since the iterative solution can omit any of the values other than 1, 0, and −1.

Figure 10:
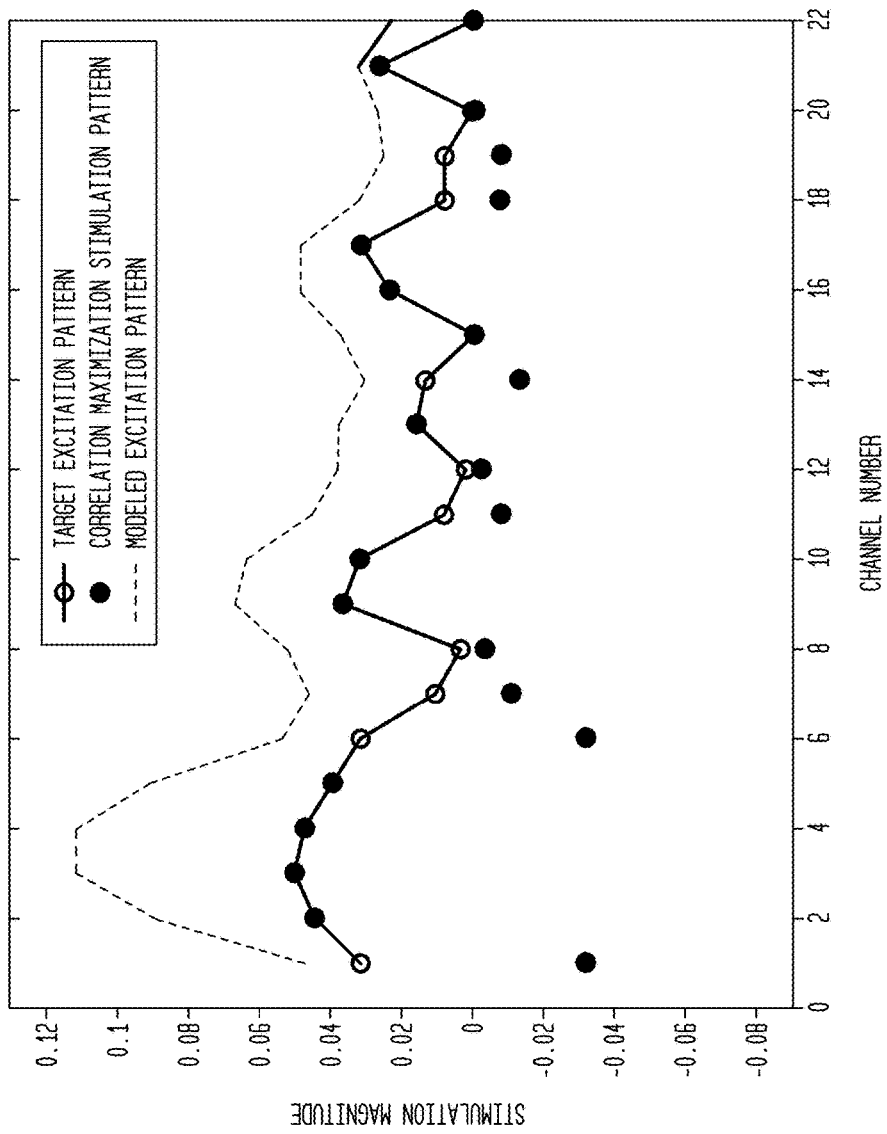
FIG. 10 is a graph illustrating another modeled excitation pattern that is correlated to a target excitation pattern in accordance with embodiments presented herein.

FIG. 10 is a graph 1000 illustrating a target excitation pattern 1002, a modeled excitation pattern 1004, and a resulting stimulation pattern (correlation maximization stimulation pattern) 1006 determined through the correlation maximization techniques of Equation 7. The target excitation pattern 1002, modeled excitation pattern 1004, and the correlation maximization stimulation pattern 1006 are represented in FIG. 10 as plots of stimulation magnitudes at corresponding stimulation channels.

In the example of FIG. 10, the cochlear implant has the ability to simultaneously deliver positive and negative currents, but the possible weighting values are −1, 0, and 1. By maximizing the cost function of Equation 7, channel magnitudes representing a received sound are either selected or not selected to generate the correlation maximization stimulation pattern 1006. In this way, the correlation maximization stimulation pattern 1006, when delivered to the recipient's auditory system, evokes an excitation pattern (represented by modeled excitation pattern 1004) having a shape that approximately matches the shape of the target excitation pattern 1002 (i.e., substantially retains the spectral information present in the target excitation pattern).

As noted above, optimal solutions of the correlation maximization cost functions could be obtained by simultaneously solving for the various values of the channel weighting vectors. Such a simultaneous stimulation solution may have a computational cost that makes it difficult to implement in a real-time system. As such, iterative solutions may be implemented to reach a result that approximates the optimal solution. It is to be appreciated that a number of different iterative solutions may be utilized.

Figure 11A:
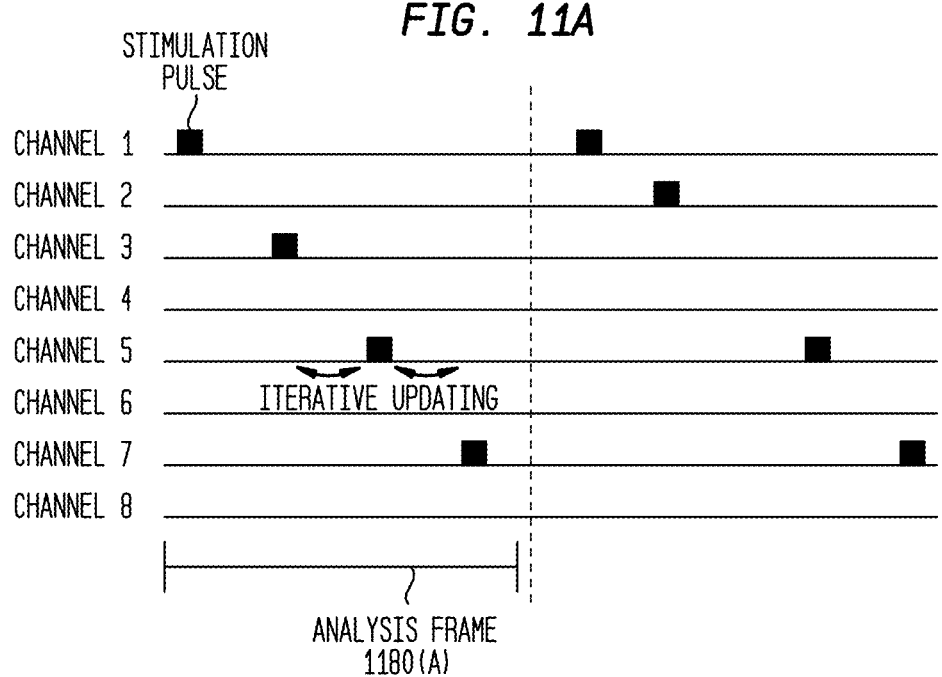
FIGS. 11A and 11B are timing diagrams illustrating analysis frames in accordance with embodiments presented herein.

For example, FIG. 11A illustrates one iterative solution that can use a cycle in which the channel weights are evaluated sequentially (i.e., an iterative process that solves the cost function for each channel one-by-one) to determine whether use of the corresponding stimulation channel improves correlation. In this solution, n number of channel weights are selected. As such, an "analysis frame" 1180(A) comprises a time frame in which a plurality of channel magnitudes are selected and delivered via one of the n stimulation channels. In the specific embodiment of FIG. 11A, eight (8) total channels are present and four (4) channels are selected within each analysis frame 1180(A).

Figure 11B:
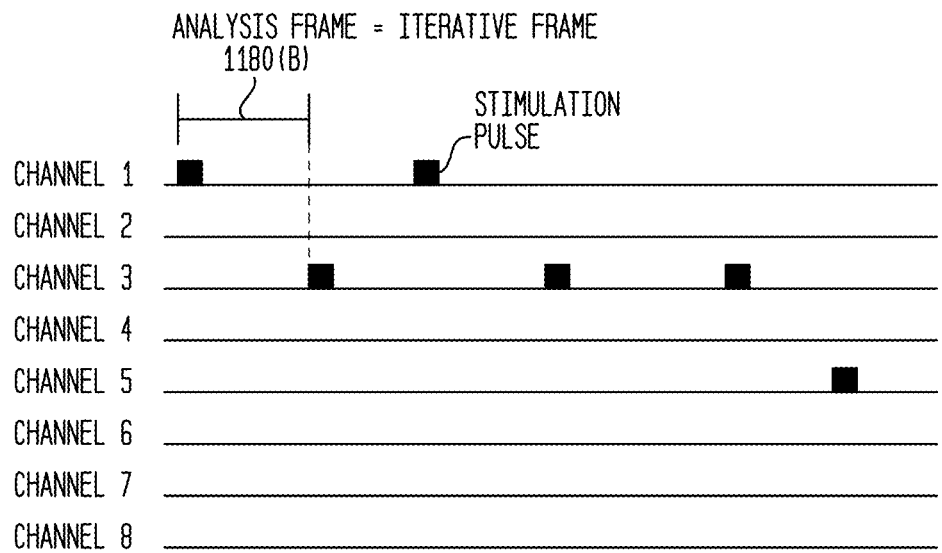

FIG. 11B illustrates an alternative iterative solution that alters the "analysis frame" to include the selection and delivery of only a single stimulation signal at a corresponding stimulation channel. Within each of these singular analysis frames 1180(B), sometimes referred to herein as "iterative frames," the stimulation channel (among all of the other channels) that produces maximum correlation of the modeled excitation pattern with the target excitation is selected for use in delivering stimulation to the recipient. In accordance with this iterative process, the same channel can be selected for delivery of sequential stimulation signals (e.g., in the cases of a pure tone signal). This reduces computation costs as it is easier to select one channel at a time. This solution is possible because the algorithm in place has knowledge of the previous frame and is aware of the neural response of the auditory system. As such, the techniques can perform the stimulation channel selection from scratch in each new analysis frame. The time period of the analysis frame is different in each of the two above noted iterative solutions.

Embodiments presented herein result in the modification of channel magnitudes (i.e., weighting channel magnitudes) in a manner that maximizes correlation between a modeled excitation pattern and a target excitation pattern. In certain embodiments, a determination may be added as to whether a modification should be implemented. For example, in an embodiment where a single stimulation channel is selected in each analysis frame, a threshold level of "correlation improvement" may be met before the stimulation is delivered on the stimulation channel. The "correlation improvement threshold" is a lower limit on how much delivery of the stimulation signal is likely to improve the correlation. The correlation improvement threshold may be a minimum correlation improvement of, for example, 1%, 10%, etc. If delivery of the stimulation signal is estimated to provide a correlation improvement that falls below the threshold, then the stimulation signal may not be delivered to the recipient. Use of such an improvement correlation threshold may conserve energy by omitting stimulation signals that do not cause sufficient improvements in correlation.

FIG. 12 is a flowchart of a method 1250 in accordance with embodiments presented herein. The method 1250 begins at 1252 where a target excitation pattern for perception of a received input (e.g., sound) at a recipient's perceptual system (e.g., auditory system, visual system, etc.) is determined. At 1254, a modeled excitation pattern for the recipient's perceptual system is modeled. The modeled excitation pattern corresponds to delivery of stimulation current representative of the received input to the recipient's perceptual system and a biological response (e.g., neural response) of the recipient's perceptual system resulting from delivery of the stimulation current. At 1256, the modeled excitation pattern is correlated with the target excitation pattern to generate a pattern of stimulation current configured to evoke an excitation pattern within the recipient's perceptual system that approximates the shape of the target excitation pattern. At 1258, the pattern of stimulation current is delivered to the recipient.

In certain embodiments, correlating the modeled excitation pattern with the target excitation pattern comprises maximizing a correlation of the modeled excitation pattern with the target excitation pattern in accordance with a cost function. The cost function may include a channels weights vector comprised of a plurality of values each corresponding to a weighted level of stimulation current for delivery to the recipient's auditory system via a corresponding stimulation channel. The method 1250 may further comprise iteratively adjusting one or more of the values in the channel weights vector to identify levels of stimulation current that maximize the correlation between the modeled excitation pattern and the target excitation pattern.

Figure 13:
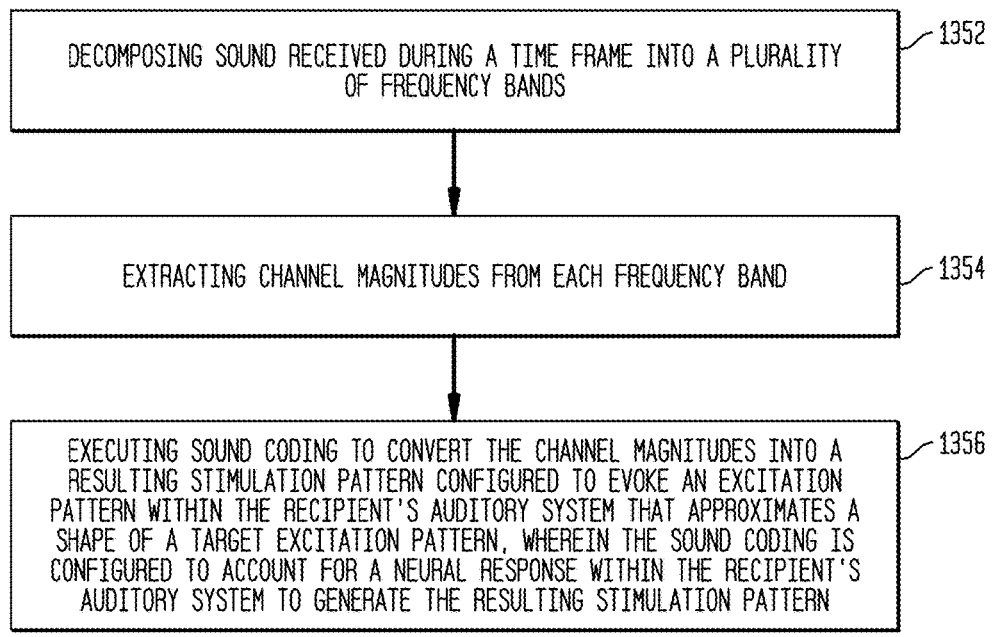
FIG. 13 is a flowchart of another method in accordance with embodiments presented herein.

FIG. 13 is a flowchart of another method 1350 in accordance with embodiments presented herein. Method 1350 begins at 1352 where sound received during a time frame is decomposed into a plurality of frequency bands. At 1354, a channel magnitude is selected from each frequency band. At 1356, sound coding is executed to convert the channel magnitudes into a resulting stimulation pattern configured to evoke an excitation pattern within the recipient's auditory system that approximates a shape of a target excitation pattern. The sound coding is configured to account for a neural response within the recipient's cochlea to generate the resulting stimulation pattern.

In one embodiment, executing the sound coding comprises generating a modeled excitation pattern corresponding to a combination of stimulation signals representative of the received sound and an estimated or predetermined neural response evoked in the recipient's auditory system as a result of delivery of the stimulation signals representative of the received sound, and correlating the modeled excitation pattern with the target excitation pattern to generate the resulting stimulation pattern. Correlating the modeled excitation pattern with the target excitation pattern may comprise maximizing a correlation of the modeled excitation pattern with the target excitation pattern in accordance with a cost function. In certain embodiments, correlating the modeled excitation pattern with the target excitation pattern comprises maximizing a correlation of the modeled excitation pattern with the target excitation pattern in accordance with a cost function that accounts for a predetermined recipient-specific spread of excitation. In other embodiments, correlating the modeled excitation pattern with the target excitation pattern comprises maximizing a correlation of the modeled excitation pattern with the target excitation pattern in accordance with a cost function that accounts for an estimated linear and symmetric spread of excitation.

Figure 14:
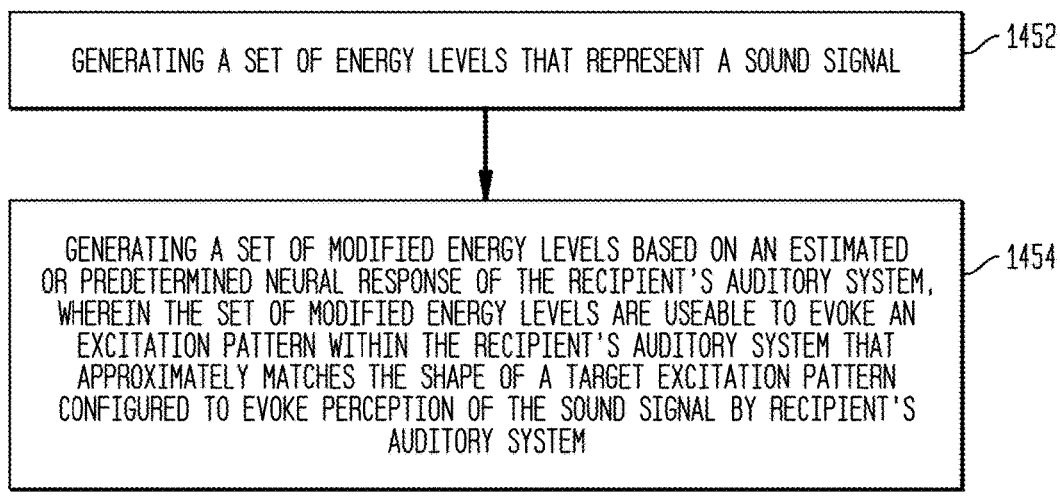
FIG. 14 is a flowchart of another method in accordance with embodiments presented herein.

FIG. 14 is a flowchart of a still other method 1450 in accordance with embodiments presented herein. Method 1450 begins at 1452 where a set of energy levels representing a sound signal is generated. Each energy level can be used as a basis for delivering stimulation current to a recipient's auditory system. At 1454, a set of modified energy levels is generated based on an estimated or predetermined neural response of the recipient's auditory system. The set of modified energy levels is useable to evoke an excitation pattern within the recipient's auditory system that approximately matches the shape of a target excitation pattern configured to evoke perception of the sound signal by recipient's auditory system.

In certain embodiments, the set of modified energy levels is generated by selecting a subset of the set of energy levels. In other embodiments, the set of modified energy levels is generated by adjusting one or more of the energy levels in the set of energy levels.

In certain embodiments, the set of modified energy levels is generated based on an estimated or predetermined spread of excitation within the recipient's auditory system. In further embodiments, the set of modified energy levels is generated based on an estimated or predetermined refractory behavior of the recipient's auditory system.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for stimulating a recipient's auditory system, comprising:
   receiving sound during a time frame;
   decomposing the received sound into a plurality of frequency bands;
   extracting channel magnitudes from each of the plurality of frequency bands;
   determining a target excitation pattern for perception of the sound by the recipient's auditory system;
   determining a modeled excitation pattern corresponding to a combination of stimulation signals representative of the received sound and an estimated neural response likely to be evoked in the recipient's auditory system as a result of delivery of the stimulation signals representative of the received sound to the recipient's auditory system;
   executing a correlation maximization process to maximize a correlation of the modeled excitation pattern with the target excitation pattern;
   based on the correlation maximization process, modifying the channel magnitudes to generate a resulting stimulation pattern configured to evoke an excitation pattern within the recipient's auditory system that approximates a shape of the target excitation pattern; and
   delivering the resulting stimulation pattern to the recipient's auditory system.

2. The method of claim 1, wherein executing a correlation maximization process to maximize a correlation of the modeled excitation pattern with the target excitation pattern comprises:
   maximizing a correlation of the modeled excitation pattern with the target excitation pattern in accordance with a cost function.

3. The method of claim 2, wherein the cost function accounts for one of a recipient-specific spread of excitation and an estimated linear and symmetric spread of excitation.

4. The method of claim 2, further comprising:
   maximizing the cost function using a Pearson correlation.

5. The method of claim 2, wherein maximizing a correlation of the modeled excitation pattern with the target excitation pattern in accordance with a cost function comprises:
   maximizing a correlation of the modeled excitation pattern with the target excitation pattern in accordance with a cost function given as:

$$J(W) = Corr\{E_t, SOE \times (E_t \cdot W) + \alpha \times EE_{(t-1)}\}$$

where $0 \leq W \leq 1$, $E_t$ is the channel magnitudes, SOE is an excitation spread matrix, $\alpha$ is an attenuation constant, and $EE_{(t-1)}$ is the channel magnitudes from a previous time frame.

6. The method of claim 2, wherein maximizing a correlation of the modeled excitation pattern with the target excitation pattern in accordance with a cost function comprises:
   maximizing a correlation of the modeled excitation pattern with the target excitation pattern for a selected number (n) channels in accordance with a cost function given as:

$$J(W) = Corr\{E_t, SOE \times (E_t \cdot W) + \alpha \times EE_{(t-1)}\}$$

where, $W \in \{0, 1\}$, $\Sigma W = n$, $E_t$ is the channel magnitudes, SOE is an excitation spread matrix, $\alpha$ is an attenuation constant, and $EE_{(t-1)}$ is the channel magnitudes from a previous time frame.

7. The method of claim 2, wherein maximizing a correlation of the modeled excitation pattern with the target excitation pattern in accordance with a cost function comprises:

maximizing a correlation of the modeled excitation pattern with the target excitation pattern in accordance with a cost function given as:

$$J(W)=Corr\{E_p SOE \times (E_t \cdot W) + \alpha \times EE_{(t-1)}\}$$

where W is a real number, $E_t$ is the channel magnitudes, SOE is an excitation spread matrix, $\alpha$ is an attenuation constant, and $EE_{(t-1)}$ is the channel magnitudes from a previous time frame.

8. The method of claim 1, wherein the channel magnitude extracted from each frequency band has an associated stimulation channel and level of stimulation current, and wherein modifying the channel magnitudes based on the correlation maximization process comprises:
 selecting only a subset of the stimulation channels for delivery of stimulation current to improve correlation of the modeled excitation pattern with the target excitation pattern.

9. The method of claim 1, wherein the channel magnitude extracted from each frequency band has an associated stimulation channel and level of stimulation current, and wherein modifying the channel magnitudes based on the correlation maximization process comprises:
 adjusting one or more of the associated levels of stimulation current to improve correlation of the modeled excitation pattern with the target excitation pattern.

10. The method of claim 1, wherein the channel magnitude extracted from each frequency band has an associated stimulation channel and level of stimulation current, and wherein modifying the channel magnitudes based on the correlation maximization process comprises:
 selecting a single stimulation channel that most maximizes correlation of the modeled excitation pattern with the target excitation pattern.

11. The method of claim 1, wherein the neural response is one or both of a spread of excitation and a refractory behavior of nerve cells within the auditory system.

12. The method of claim 1, wherein the shape of the target excitation pattern corresponds to a shape of the extracted channel magnitudes.

13. A method for stimulating a recipient's auditory system, comprising:
 receiving a sound signal;
 determining a target excitation pattern for perception of the sound signal by the recipient's auditory system;
 determining a modeled excitation pattern corresponding to a combination of stimulation signals representative of the received sound signal and an estimated neural response likely to be evoked in the recipient's auditory system as a result of delivery of the stimulation signals representative of the received sound signals to the recipient's auditory system;
 executing a correlation maximization process to maximize a correlation of the modeled excitation pattern with the target excitation pattern and determine an output stimulation pattern configured to evoke an excitation pattern within the recipient's auditory system that approximates a shape of the target excitation pattern; and
 delivering the output stimulation pattern to the recipient's auditory system.

14. The method of claim 13, wherein executing a correlation maximization process to maximize a correlation of the modeled excitation pattern with the target excitation pattern comprises:
 maximizing a correlation of the modeled excitation pattern with the target excitation pattern in accordance with a cost function.

15. The method of claim 14, wherein the cost function accounts for one of a recipient-specific spread of excitation and an estimated linear and symmetric spread of excitation.

16. The method of claim 14, further comprising:
 maximizing the cost function using a Pearson correlation.

17. The method of claim 14, wherein executing a correlation maximization process to maximize a correlation of the modeled excitation pattern with the target excitation pattern comprises:
 maximizing a correlation of the modeled excitation pattern with the target excitation pattern in accordance with a cost function given as:

$$J(W)=Corr\{E_p SOE \times (E_t \cdot W) + \alpha \times EE_{(t-1)}\}$$

where $0 \leq W \leq 1$, $E_t$ is the channel magnitudes, SOE is an excitation spread matrix, $\alpha$ is an attenuation constant, and $EE_{(t-1)}$ is the channel magnitudes from a previous time frame.

18. The method of claim 14, wherein maximizing a correlation of the modeled excitation pattern with the target excitation pattern in accordance with a cost function comprises:
 maximizing a correlation of the modeled excitation pattern with the target excitation pattern for a selected number (n) channels in accordance with a cost function given as:

$$J(W)=Corr\{E_p SOE \times (E_t \cdot W) + \alpha \times EE_{(t-1)}\}$$

where, $W \in \{0, 1\}$, $\Sigma W = n$, $E_t$ is the channel magnitudes, SOE is an excitation spread matrix, $\alpha$ is an attenuation constant, and $EE_{(t-1)}$ is the channel magnitudes from a previous time frame.

19. The method of claim 14, wherein maximizing a correlation of the modeled excitation pattern with the target excitation pattern in accordance with a cost function comprises:
 maximizing a correlation of the modeled excitation pattern with the target excitation pattern in accordance with a cost function given as:

$$J(W)=Corr\{E_p SOE \times (E_t \cdot W) + \alpha \times EE_{(t-1)}\}$$

where W is a real number, $E_t$ is the channel magnitudes, SOE is an excitation spread matrix, $\alpha$ is an attenuation constant, and $EE_{(t-1)}$ is the channel magnitudes from a previous time frame.

20. The method of claim 13, wherein the neural response is one or both of a spread of excitation and a refractory behavior of nerve cells within the auditory system.

* * * * *

UNITED STATES PATENT AND TRADEMARK OFFICE
CERTIFICATE OF CORRECTION

PATENT NO. : 9,999,769 B2  
APPLICATION NO. : 14/324388  
DATED : June 19, 2018  
INVENTOR(S) : Qazi et al.

Page 1 of 1

It is certified that error appears in the above-identified patent and that said Letters Patent is hereby corrected as shown below:

On the Title Page

In Item (73) Assignee, please change "Cisco Technology, Inc., San Jose, CA (US)" to --Cochlear Limited, Macquarie University, NSW (AU)--

Signed and Sealed this
Seventeenth Day of July, 2018

Andrei Iancu
*Director of the United States Patent and Trademark Office*